United States Patent
Mead, III et al.

(10) Patent No.: US 6,235,015 B1
(45) Date of Patent: *May 22, 2001

(54) METHOD AND APPARATUS FOR SELECTIVE HAIR DEPILATION USING A SCANNED BEAM OF LIGHT AT 600 TO 1000 NM

(75) Inventors: Douglass S. Mead, III, Allendale; Thomas Cekoric, Jr., Lambertville, both of NJ (US)

(73) Assignee: Applied Optronics Corporation, South Plainfield, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/076,466

(22) Filed: May 12, 1998

Related U.S. Application Data (60) Provisional application No. 60/046,465, filed on May 14, 1997, and provisional application No. 60/057,048, filed on Aug. 22, 1997.

(51) Int. Cl.[7] ................................................ A61B 18/18

(52) U.S. Cl. .................................................... 606/9

(58) Field of Search ........................ 606/8, 9, 10, 11, 606/12, 13, 14, 15, 16, 17

(56) References Cited

U.S. PATENT DOCUMENTS

| | | |
|---|---|---|
| 3,538,919 | 11/1970 | Meyer . |
| 4,388,924 | 6/1983 | Weissman et al. . |
| 4,608,978 | 9/1986 | Rohr . |
| 4,617,926 | 10/1986 | Sutton . |
| 5,059,192 | 10/1991 | Zalas . |
| 5,182,857 * | 2/1993 | Simon .................................... 606/9 |
| 5,226,907 | 7/1993 | Tankovitch . |
| 5,336,217 * | 8/1994 | Buys et al. ............................ 606/9 |
| 5,425,728 | 6/1995 | Tankovitch . |
| 5,474,549 * | 12/1995 | Ortiz et al. ............................ 606/9 |

(List continued on next page.)

FOREIGN PATENT DOCUMENTS

WO 93/13723   6/1993   (WO) .

Primary Examiner—Linda C. M. Dvorak
Assistant Examiner—S. Harris-Ogugua
(74) Attorney, Agent, or Firm—Eitan, Pearl, Latzer & Cohen-Zedek (57) ABSTRACT

An apparatus and method for hair depilation using a beam of light, preferably a scanned continuous output diode laser beam, operating primarily in a range of wavelengths from 650–1000 nanometers is disclosed. The beam of light is focused by a handpiece such that the power density and energy density of the beam is sufficient for selective coagulation of dermal melanosomes and destruction of hair follicles adjacent to melanosomes. The beam is directed over the treatment area by any type of motorized mirror and lens-based scanning device such that the duration of exposure to the treatment area is limited to a fixed time interval according to the velocity of the beam moving across the treatment area, or a specified dwell time whereby the scanned beam is held at each position in the scan for a specified time duration, preferably in a pseudo-random sequence. The scanner connects to a contact member, at least a portion of which is held in contact with the skin, to provide a fixed focus and surface contact cooling. The scanned beam velocity or dwell time, focal spot size, and output power therefore determine the energy and energy density at each location within a scanned area. This method provides for selective coagulation by wavelength absorption which is enhanced by differential cooling using high energy, short duration exposure produced by a scanned laser beam which can be performed with a wide variety of available laser beam scanners and with continuous output diode or other lasers of suitable wavelengths.

27 Claims, 4 Drawing Sheets

U.S. PATENT DOCUMENTS

| | | |
|---|---|---|
| 5,486,172 * | 1/1996 | Chess .......................................... 606/9 |
| 5,595,568 | 1/1997 | Anderson et al. . |
| 5,630,811 | 5/1997 | Miller . |
| 5,647,866 | 7/1997 | Zaias et al. . |
| 5,683,380 | 11/1997 | Eckhouse et al. . |
| 5,735,844 * | 4/1998 | Anderson et al. ........................ 606/9 |
| 5,807,386 * | 9/1998 | Slatkine et al. ........................... 606/9 |
| 5,810,801 * | 9/1998 | Anderson et al. ........................ 606/9 |
| 5,868,732 | 2/1999 | Waldman et al. . |
| 5,879,346 | 3/1999 | Waldman et al. . |
| 5,885,273 | 3/1999 | Eckhouse et al. . |

* cited by examiner

METHOD AND APPARATUS FOR SELECTIVE HAIR DEPILATION USING A SCANNED BEAM OF LIGHT AT 600 TO 1000 NM

This application claims the benefit of U.S. Provisional Application Ser. No. 60/046,465, filed May 14, 1997, entitled "Method of Selective Hair Depilation Using a Scanned Laser Beam" and U.S. Provisional Application Ser. No. 60/057,048, filed Aug. 22, 1997, entitled "Method of Selective Hair Depilation Using a Scanned Laser Beam at 650–830 nm."

FIELD OF THE INVENTION

This invention relates to the use of a scanned beam of light to provide a method and apparatus for hair depilation. In particular, this invention relates to the use of a scanned beam of light to provide selective coagulation of targeted structures while limiting coagulation of nontargeted structures.

BACKGROUND OF THE INVENTION

Permanent or long term hair removal for cosmetic reasons has been accomplished by various methods. For example, hair can be removed by heating the hair and the hair follicle to a high enough temperature that results in coagulation. It is known that blood is coagulated when heated to temperatures on the order of 50–70° C. Heating of the epidermis, the hair and the hair follicle to temperatures on the same order of magnitude will cause coagulation in the epidermis as well as the hair follicle and will result in permanent or long term removal of the hair with the unwanted result of scarring.

One common method of hair removal without scarring, often called electrolysis, is based on the use of "electric needles" that applies electric current to each hair through the needle. The current heats the hair and not the epidermis, causes its carbonization and also causes coagulation of the tissue adjacent to the hair as well as some coagulation of the micro-vessels that feed the hair follicle. While the electric needle method can remove hair permanently or long term without scarring, its use is practically limited because the treatment is painful and the procedure is generally tedious and lengthy.

Light can also be used effectively to remove hair. For example, prior art methods of hair removal involve the application of pulsed light. R. A. Harte, et al., in U.S. Pat. No. 3,693,623, and C. Block, in U.S. Pat. No. 3,834,391, teach hair removal by coagulating individual hairs with a light coupled to the individual hair by an optical fiber at the immediate vicinity of the hair. Similarly, R. G. Meyer, in U.S. Pat. No. 3,538,919, removes hair on a hair by hair basis using energy from a pulsed laser. A similar invention using small fibers is described in U.S. Pat. No. 4,617,926 to A. Sutton.

A wide variety of lasers have been used in dermatological applications for treatment of such conditions as vascular lesions (e.g. hemangiomas), pigmented lesions (e.g., nevi), tattoo removal, lentigines, cafe-au-lait macules, and other skin conditions and lesions. Through the principles of selective photothermolysis, specific wavelengths of light are known to be absorbed to a greater or lesser degree in certain skin pigments, tattoo inks, heme (blood pigment) or other chromophores. Wavelength selection also allows the targeting of these pigments and related structures at various depths within the dermis based on the magnitude of total absorption and light scattering as a function of depth.

Selective coagulation by wavelength absorption requires that the light energy used has a wavelength that is preferentially absorbed by the target structure or tissue. It also requires that a high enough power be used to cause tissue damage and that the heat be absorbed in the target structures faster than it is dissipated to surrounding tissue.

U.S. Pat. No. 4,388,924 to H. Weissman, et al. discloses a system wherein a narrow, focused beam of light is aimed at the epidermis adjacent to the hair such that an extension of the beam intersects the hair root at an angle relative to the skin's surface. A pulse, disclosed as a short pulse of less than 400 milliseconds but more than 10 milliseconds, passes through the skin and is selectively absorbed in the hair root destroying its blood supply.

The Weissman patent discloses apparatus which employs a manually controlled two-axis positioning system supporting the focusing system that is connected to a laser light source, preferably argon, by a flexible fiber optic bundle. The argon beam has most of its energy in the wavelength range of 482–520 nanometers. The Weissman patent further discloses that light of that wavelength passes through relatively light human skin without any appreciable absorption yet is highly absorbed in a dark hair root. Thus, the Weissman patent discloses selective coagulation by light absorption as a function of wavelength. The thermal energy produced upon absorption of the light energy within the hair root causes coagulation of the blood vessels and destroys the hair root. The hair body is generally vaporized in the process. Finally, Weissman claims that the process is relatively painless to the patient because of the low degree of absorbency and short pulse within the dermis.

The above prior art techniques suffer from a number of limitations. First, techniques for irradiating an individual hair follicle are time consuming and, therefore, not generally practical for removing hairs other than from a very small region or from a region having few hairs situated therein. The procedure can also be painful, particularly if a needle-like element is inserted in the hair follicle to facilitate light energy reaching the bulge and the root or papilla, which are the parts of the hair follicle which must be destroyed in order to prevent regrowth of the hair. Furthermore, it is difficult to get sufficient energy at the wavelength described to the required portions of the follicle to cause destruction thereof without also causing significant damage to the surrounding tissue and, thus, causing pain and injury to the patient.

Using the principles of selective coagulation by wavelength absorption or photothermolysis, certain laser wavelengths at short pulse durations (several picoseconds through several milliseconds) have been shown to have therapeutic benefits for specific types of lesions or treatments. For example, the flash-lamp-pumped, pulsed dye laser radiation at 585 nm is selectively absorbed by hemoglobin in capillary beds and small blood vessels and is used to treat vascular lesions such as hemangiomas. While shorter wavelengths (e.g., 532 nm) are also selectively absorbed by blood and can be used, they do not penetrate as deeply in the lesion as the 580–590 nm units and are sometimes less effective in thicker lesions. The Q-switched ruby (694 nm), alexandrite (755 nm) and neodymium: YAG (1064 nm) lasers have increasingly longer wavelengths, are deeper-penetrating and are absorbed preferentially by melanin rather than hemoglobin. These pulsed lasers are therefore used to treat pigmented lesions (e.g., nevus of Oti) and tattoo inks of dark colors. The $CO_2$ laser, in contrast to the above lasers, is absorbed by the water content in tissue and is therefore non-selective by colors. One example of $CO_2$ laser use in dermatology is for superficial skin vaporization (cosmetic skin resurfacing)

using a high-energy, short-pulsed output or a scanned continuous-output laser beam.

High-power diode lasers can now produce radiation at wavelengths of 650–700 nm, 730–1000 nm and 1880–1960 nm. Diodes are available in a wide choice of wavelengths and are efficient converters of electrical energy to light. Some diode laser outputs can be pulsed (e.g., picosecond to nanosecond) like the above solid state lasers but they cannot practically produce the very high peak power (e.g., 20–1,000 kilowatts) needed to achieve selective coagulation by wavelength absorption without unwanted tissue injury.

Treatment of pigmented skin lesions based on selective coagulation by wavelength absorption or photothermolysis has been performed using the Q-switched ruby laser, the Q-switched Nd: YAG laser and the Q-switched alexandrite laser. With these lasers, a high peak power output with a very short duration selectively vaporizes melanin-containing cells. That is, the melanin-containing cells are vaporized with minimal damage to underlying, overlying or adjacent cells. These laser types have a pulse duration too short for optimal effects on larger cellular structures such as hair follicles.

U.S. Pat. No. 5,344,418 to S. Ghaffari discloses an optical system for treatment of skin disorders resulting from blood vessels in the dermis which minimizes damage to epidermal and dermal layers which light must pass through by including a temperature compensation and monitoring system. That system reportedly cools the skin to temperatures as low as 5° C. Specifically, the light, which is from an incoherent source, is passed to a sapphire lens contained in the tip of a conical housing, which includes channels for transporting cooling gas to the sapphire lens. The sapphire lens is placed in contact with the surface of the skin to be treated.

The system disclosed in the Ghaffari patent irradiates the skin and cools the skin during a predetermined time interval in coordination with the delivery of the radiation. The absorption of the radiation by the skin and the change in temperature of the skin is monitored by the system. The operation of the radiation delivery system is controlled to optimize treatment of deep lying vascular lesions. Therefore, the Ghaffari patent discloses selective coagulation enhanced by differential cooling and, as a result, differential heat by the radiation to promote the selective treatment of deep lying vascular lesions. In comparison, the Weissman patent and other patents teaches the selective absorption of radiation to selectively coagulate (i.e., selective coagulation by wavelength absorption) hair follicles and not skin without enhancement by differential cooling.

A disadvantage of the Ghaffari system is that only the skin being irradiated is cooled. The sapphire lens provides focusing of the beam at the point of contact to the skin and the lens requires cooling in its entirety since the light beam is large in comparison to the lens diameter. Therefore, in that system, only treated skin, and not skin adjacent to the treated area, is cooled. U.S. Pat. No. 5,059,192 to Zaias disclosed a method of hair depilation using a ruby red laser. The method disclosed is for treatment of a single or group of hairs while causing minimal damage to the skin. The Zaias patent discloses use of a Q-switched ruby laser with an output at 694 nm, pulse energies from 0.4 to 10 joules/cm$^2$ and pulse durations of 3040 nanoseconds. This output causes melanosomes adjacent to the base of the hair follicle to rupture due to the rapid high absorption of laser energy, heat production and vaporization of the melanosomes.

More recently, a normal-mode ruby laser has been shown to be effective in hair removal in an article entitled "Damage to Hair Follicles by Normal-Mode Ruby Laser Pulses" by Melanie C. Grossman, M.D., et al., *J Amer Acad Dermatology*, Vol. 35, No.6, pp. 889–894, 1996. In a controlled study, a beam was used that had a diameter of 6 mm and a pulse length of 270 microseconds, emitting from 30–60 joules/cm$^2$. Selective photothermolysis was demonstrated, producing prolonged hair growth delay or, in some cases, permanent hair removal. The authors further report that they designed a delivery device which appears to be quite similar to that disclosed in the Ghaffari patent to optimize deep light delivery and limit epidermal injury. Similar to the Ghaffari patent, this included a convergent beam at the skin, a large exposure spot diameter, and a forceful compression of the skin to eliminate blood, deform the dermis and reduce the distance between the surface and the hair. The device was cooled to extract more heat from the dermis on contact.

The device and method of the Grossman article appears to be similar to the subject matter of U.S. Pat. Nos. 5,595,568 and 5,735,844 to Andersen, et al. In the '844 patent, radiation of a selected wavelength is applied through an applicator in contact with the skin for a predetermined time. As in the Ghaffari patent, the applicator is preferably a sapphire lens designed to converge optical radiation applied to the skin (i.e., a lens) and has a means for cooling. Also as in the Ghaffari patent, a sapphire or diamond lens is preferred because of their high thermal conductivity and transparency to visible light. However, the system disclosed in the '844 patent and the Grossman article has the same disadvantages as the Ghaffari patent.

High-peak-power radiation from a pulsed $CO_2$ laser has been used for predictable vaporization of tissue, either for incision of tissue or for bulk ablation. Furthermore, as an alternative to using a high-energy pulsed $CO_2$ laser, scanning a continuous-output high-power-density laser beam within a specified area has also been used with the $CO_2$ laser. This provides a means for controlling localized laser exposure over very short time durations, resulting in predictable vaporization of tissue.

At least three scanners which move a beam of light in a controlled fashion have been commercialized for use with the continuous-wave $CO_2$ laser including one sold under the trademark Sharplan Lasers Silktouch Scanner, another sold under the trademark Reliant Lasers Accuscan Scanner and another sold under the trademark SAHAR Technologies Scanner. Applications with these scanners and the $CO_2$ laser include uvulopalatoplasty, skin resurfacing and production of cylindrical puncture sites for hair or skin transplantation. Further, Sharplan commercializes a scanner for use with an alexandrite laser for hair depilation. That system utilizes 2 millisecond pulses with 5–10 millimeter spot sizes over 5×5 centimeter areas. That scanner utilizes a ring with a metal perimeter pointer for stable positioning. While there is contact between the scanner and the skin for stable positioning, there is no cooling of the scanner or the skin as part of the assembly design.

U.S. Pat. No. 5,411,502 to E. Zair, et al., shows high-velocity scanning of a high-intensity laser beam over a defined area to be a very effective method of limiting tissue exposure to individual areas within the scanned areas. The net tissue vaporization effects and avoidance of unwanted thermal injury using scanned continuous, low-average-power, laser outputs, have been proven to be comparable to $CO_2$ lasers that produce pulses of high peak power (500–1,000 watts) for short duration (0.5–4 millisecond) over the same treatment area.

Longer exposures (up to 100 milliseconds) at lower fluences, such as those produced by the scanned continuous output of a diode laser, result in advantageous selective coagulation by wavelength absorption and denaturation of protein within the melanocytes. This selective coagulation is a subset of selective photothermolysis which does not rely upon vaporization and high temperature gaseous effects.

One condition of selective photothermolysis and coagulation enhanced by differential cooling as disclosed in the Ghaffari and Anderson patents and the Grossman article is that the target structure must be heated by the applied laser energy at a rate faster than its rate for cooling. This concept is referred to as thermal relaxation time. The thermal relaxation time of melanosomes has been postulated to range from 250 nanoseconds to one microsecond based on the size of these structures. However, when the total target volume includes the hair follicle and surrounding melanocytes (total diameter 200–300 microns), the estimated thermal relaxation time is 40–100 milliseconds. Importantly, while selective photothermolysis for coagulation is intended to limit thermal injury to adjacent tissue, significant thermal injury to the papilla of the hair follicle adjacent to melanosomes is required to achieve follicle damage and cessation of hair growth. It is important to note that current normal-mode Ruby laser technology has not produced outputs 45 longer than 3 milliseconds. Therefore, a laser that could produce exposures (10–75 msec) to the skin would be expected to have increased efficacy over the current laser technology consistent with other researcher's findings.

SUMMARY OF THE INVENTION

This invention is directed to a method for removing hair from skin which comprises defining an area of the skin by placing a contact member on the skin, cooling at least a portion of that contact member, generating a beam of light having a wavelength in the range of 650 nm to 1000 nm, directing the beam of light through the contact member onto the skin in that area so that the beam of light has a spot size on the skin which is substantially smaller than that area, and scanning the beam of light across the area of that skin. This invention is also directed to the related apparatus comprises a light source having a spot size and a wavelength in the range of 650 nm to 1000 nm, a contact member for providing a window for the beam of light to the skin and which has a surface area greater than the spot size of said beam of light, a scanner for moving the beam of light in a predetermined pattern on the skin through the window, and a cooling device for cooling at least a portion of the contact member. In a preferred embodiment of the invention, the light source and the scanner are connected by an optical fiber.

Preferably, the beam of light is a diode laser. It is also preferable that the beam is at a power level equal to or greater than 10 watts. In another preferred embodiment, the beam is scanned in accordance with a predetermined pattern in a pseudo-random sequence covering substantially all of, or within, a defined area.

The contact member preferably comprises a material transparent to wavelengths emitted by the beam of light and has a high thermal conductivity and capacity, such as sapphire or diamond. It is also preferable that at least a portion of the contact member is for contact with the skin.

In still another preferred embodiment, a peripheral portion of the contact member is for cooling and the interior portion is for contacting with the skin thereby providing a window for the beam of light to the skin. Preferably, there is a coupling between the peripheral portion and a thermoelectric cooler and heatsink. In that embodiment, the contact member also preferably provides an intermediate heatsink between the skin and the thermoelectric cooler.

Finally, in yet another embodiment, the location under the skin of a focus of the beam of light is controlled by a lens in the scanner. Furthermore, that lens may also provide an angle of convergence of the beam of light on the skin of at least 8.5°.

DETAILED DESCRIPTION OF THE INVENTION

An object of this invention is to provide a beam of light which is scanned in steps to deliver energy to pigments near hair follicles to coagulate the follicles and thereby destroy them. Choice of the wavelength of the beam of light, preferably a diode laser, allows the targeting of specific chromophores in the skin. Another object is to provide a surface contact cooling for the skin which is irradiated as well as the skin adjacent thereto. In this embodiment, the scanner is connected to a contact member preferably comprised of a material which is transparent to the wavelengths emitted by the beam and which has a high thermal conductivity and capacity. At least a portion of the contact member is held in contact with the skin to provide a fixed focus as well surface contact cooling. The contact member is preferably sapphire or diamond and includes (i) a peripheral portion which is in contact and cooled by a thermoelectric cooler, which can be any shape, such as square, rectangular or annular, and a heatsink, and (ii) an interior portion which is in contact with, and thus provides a window for transmission of a beam of light to, the skin. In this way, the area surrounding the irradiated spot is cooled. This provides for effective cooling not only of the skin overlying the treated area but also the skin adjacent thereto. This embodiment limits the thermal injury to the treated spot as well as adjacent tissue and structures, thereby minimizing the risk of hyper- and hypopigmentation and scarring.

Still another object of this invention is to provide the ability to predictably treat individual hair follicles as well as large areas of skin and multiple hair follicles using a scanned light beam output.

The invention is not limited in its application to the details of construction and the arrangement of the components set forth in the following description or illustrated in the drawings. The invention is capable of other embodiments or of being practiced or carried out in various ways. Also, the phraseology and terminology employed herein is for the purpose of description and should not be regarded as limiting.

Figure 1:
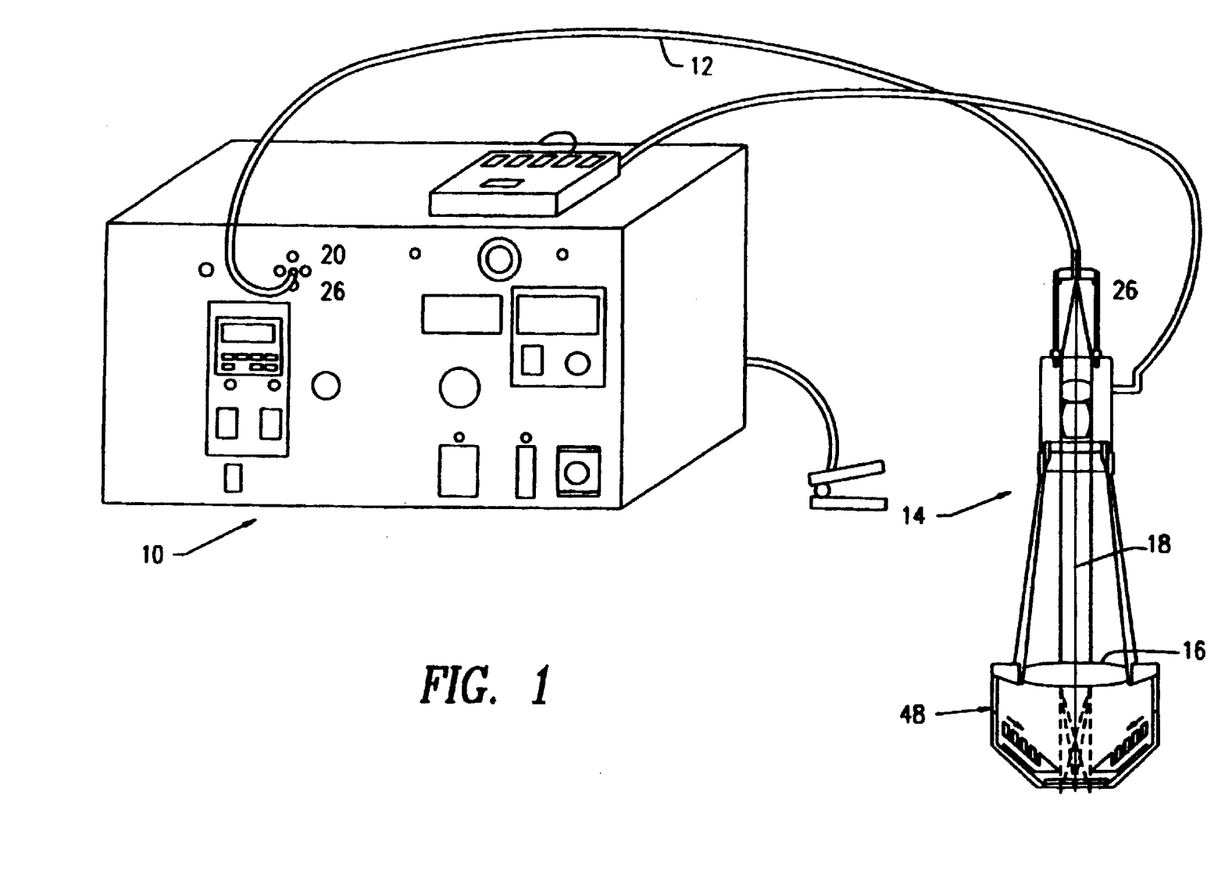
FIG. 1 is an overall block diagram of a system for the practice of the present invention.
Figure 2:
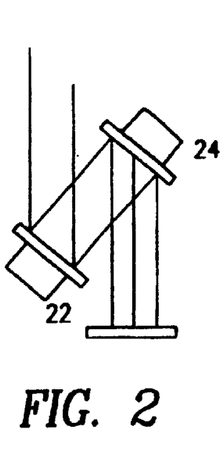
FIG. 2 is a side view of the structure of the scanning mechanism of the scanner of FIG. 1.

FIG. 1 is an overall block diagram of a system for the practice of the present invention, and FIG. 2 is a side view of the structure of the scanning mechanism of the scanner of FIG. 1.

In FIG. 1, a laser console 10 contains a laser 20 capable of producing radiation at a desired wavelength and control circuitry for the laser 20. A fiberoptic cable 12 is connected from the console 10 to a scanner 14, which is preferably handheld although it could be controlled by a mechanical and/or electrical system. A lens 16 focuses a beam 18 in the scanner 14 which converges to a desired spot size at a desired depth in or under the skin. In FIG. 2, a pair of motor-actuated mirrors 22 and 24 are controlled to scan the spot in a desired pattern, typically a sequence of steps to index the spot.

In a preferred embodiment, a diode laser 20 and scanner system 14 includes the following features shown in FIGS. 1 and 2:

1. A diode laser 20 operating at a wavelength at 650–1000 nm and capable of producing at least 10 watts of CW laser power into a fiberoptic cable 12. Because the production of a high powered diode lasers requires the selection of multiple discrete laser diode elements, exact wavelengths for each element can be selected within these ranges. A unit may include more than one laser and a user control to select a desired laser wavelength in discrete ranges such as 670 to 730 nm, 810 to 830 nm or 850 to 890 nm.

2. A fiberoptic cable 12 that interfaces or connects between the laser console 10 and the motorized, hand-held optical scanner 14. The fiberoptic cable 12 preferably is 2–3 meters long and is terminated with an SMA 905 fiberoptic connector 26 on both ends, has a single core fiber diameter of 600–1000 microns, a numerical aperture from 0.22 to 0.37 and is enclosed in a protective jacket.

3. A hand held optical scanner 14 that re-images the output from the single core fiber onto the target tissue, and controls the beam 18 within the scanner 14 using orthogonally positioned, motor driven, microprocessor controlled mirrors 22 and 24 to produce various scan patterns including square, rectangular, hexagonal, trapezoidal and line patterns over a specified area. The scanner 14 has a software adjustment for the effective dwell time of any specific location of exposure. The scanner 14 moves from target spot to target spot within 20 microseconds and can "hold" at each location for the specified dwell time. Dwell times are software programmable from 1–100 milliseconds. It is preferred that the energy be deposited in a pseudo-random fashion to prevent local buildup of heat in tissue surrounding the target spots and to increase efficiency of the differential cooling of irradiated skin. The scanner 14 may be a modified SAHAR Technologies, Inc. scanner system. The modification includes the ability to program longer dwell times than those used for conventional vaporization purposes with $CO_2$ lasers.

Figure 3:
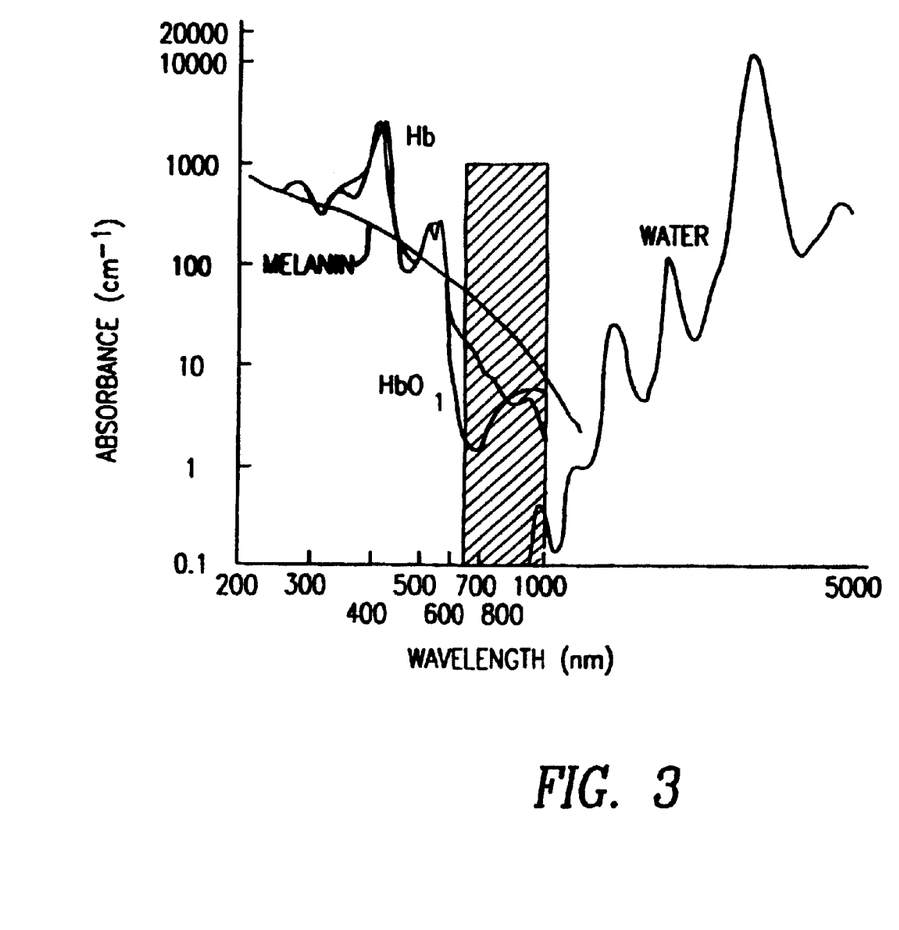
FIG. 3 is a typical absorption spectrum showing the absorbance of melanin as a function of wavelength.

FIG. 3 is a typical absorption spectrum showing the absorbance of melanin as a function of wavelength. In FIG. 3, the range of wavelengths that are of interest are those that produce preferential absorption in melanin, which is associated with hair follicles.

Figure 4:
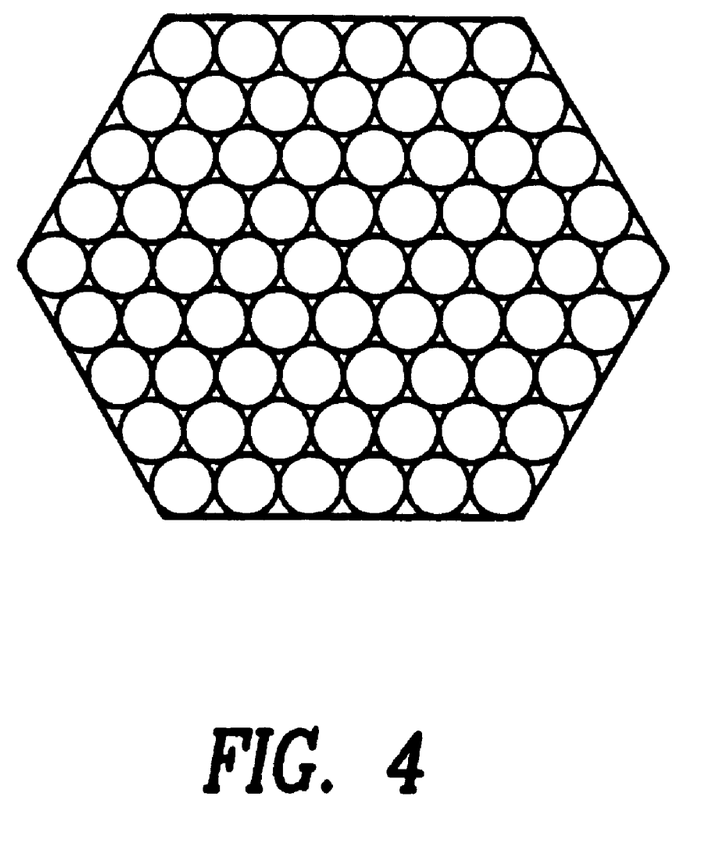
FIG. 4 is a plot of an irradiation pattern of the present invention showing stepped or randomly applied scan positions during a single pulse or a scanner-controlled continuous output.

FIG. 4 is a plot of an irradiation pattern of the present invention showing stepped scan positions during a single scan. The pattern can be seen to cover the selected area by stepping to discrete locations, preferably accomplished as a raster or pseudo-random scan. The scanner 14 controls both the position of the spot in the pattern and the time duration of the exposure.

Figure 5:
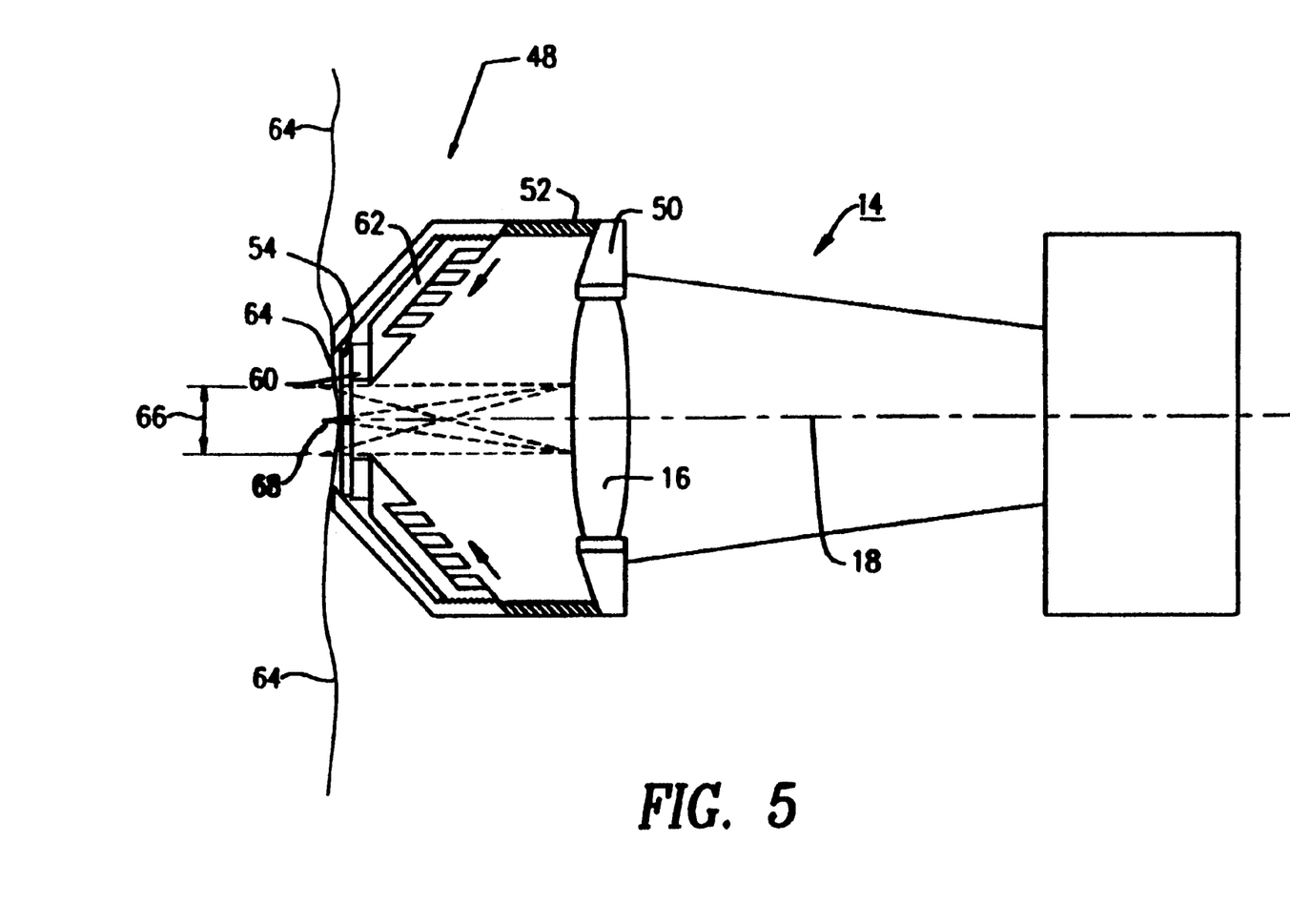
FIG. 5 is a sectional side view of the contact cooling head of the scanner of FIGS. 1 and 2 showing a thermoelectric cooler and heatsink.

FIG. 5 is a sectional side view of the contact cooling head 48 of the scanner 14 of FIGS. 1 and 2 showing a thermoelectric cooler 60 and heatsink 62. In FIG. 5, the lens 16 of FIG. 1 is supported in a thermal isolator 50 which protects the lens 16 from overheating. An open support structure 52 allows a user of the scanner 14 to view the area of skin 64 that is to be treated. The scanner system 14 is connected to a contact member 54 which is comprised of a material transparent to the wavelengths emitted by the laser 20 having a high thermal conductivity and capacity. The contact member 54, which is preferably sapphire and has sufficient thickness to act as an intermediate heatsink between the skin and the thermoelectric cooler 60, may be a sapphire window such as that sold under the trademark Tech Spec from Edmund Scientific. At least a portion of the contact member 54 is placed against the skin 64 in use. In the preferred embodiment, the contact member 54 is a sapphire disk having at least a 25 mm diameter and a 2 mm thickness such that the thermal mass thereof serves as an excellent intermediate heatsink between the skin 64 and the thermoelectric cooler 60.

The thermoelectric cooler 60 is coupled thermally to a peripheral portion of the contact member 54 to cool it and deliver heat produced in the skin 64 by the beam 18 to the heatsink 62. A second portion of the contact member 54 is not coupled to the thermoelectric cooler 60 and heatsink 62, providing a window exposing the skin 64 to the beam 18. The lens 16 is selected in combination with the dimensions of the contact cooling head 48 to focus the beam 18 at a desired depth below the surface of the skin 64.

Thus, the scanner system 14 can be modified to connect to, and thereby include, a contact member, preferably sapphire or diamond, that can be held in contact with skin 64 to provide a fixed focus as well as surface contact cooling. This design is depicted in FIG. 5. The contact member 54 is cooled using a thermoelectric cooler 60 and heatsink 62 that is thermally isolated from the handpiece of the scanner 14 by a non-thermally conductive ring isolator 50.

As an example, a scanner 14 which could aim a beam 18 having a power of 50 watts and a diameter of 2.5 mm, would produce a spot power density of 1,000 $W/cm^2$. If the scanner 14 holds that location for a precise dwell time of 40 msec., the effective energy at that location would be 40 $J/cm^2$. If the scanner 14 repeats this exposure at each location in a scanned pattern with minimal overlap and unexposed areas, the scanned area receives the same total energy dose as if that total area was exposed by a single pulse of a laser at 40 $J/cm^2$ but does so over a longer period of time allowing for more efficient heat removal. Since the scanned beam 18 deposits 2–5 joules of energy over a small spot within the scan area, the contact member 54 can easily and quickly remove the heat from each discrete spot within the scan area. The length 66 of the scan area is depicted in FIG. 5.

In a preferred embodiment, the position of the contact member 54 is fixed at a distance from the final focusing lens 16 such that the therapeutic beam 18 converges to a focal point 68 approximately 2–5 mm below the surface of the skin 64. This design has two advantages. First, the beam 18 spot size at the surface of the skin 64 is larger and the penetration loss due to light scattering phenomena is less than for a smaller diameter beam 18, as has been shown by Monte Carlo beam penetration modeling. Second, the beam 18 is converging as it penetrates the skin 64 surface rather than collimated or diverging. This has also been shown in Monte Carlo beam modeling to allow for increased depth of penetration of the light into the skin 64 and reduced intensity on the surface of the skin 64.

The convergent beam 18 used in the scanner device 14 of the present invention produces increased penetration of the beam 18 which is accomplished by prefocusing the scanner 14 lens on the skin. In the preferred embodiment, the angle of convergence is 8.5°.

As an alternate method, additional or alternative cooling of the scanner 14 and the skin 64 can be provided wherein the contact member 54 being is comprised of two individual windows enclosing a space or channels into which circulating water can be infused. Using this alternative method, the beam 18 is also prefocused to create a converging beam 18.

What is claimed is:

1. A method of removing hair from skin comprising the steps of:
   (a) defining an area of said skin by placing a contact member on said skin;
   (b) cooling at least a portion of said contact member;
   (c) generating a beam of light having a wavelength in the range of 650 nm to 1000 nm, wherein said beam of light has an angle of convergence at said skin of at least 8.5°;
   (d) directing said beam of light through said contact member onto said skin in said area so that said beam of light has a spot size on said skin which is substantially smaller than said area; and
   (e) scanning said beam of light across said area of said skin.

2. The method of claim 1 wherein said contact member is comprised of a material that is transparent to wavelengths emitted by said beam of light and has a high thermal conductivity and capacity.

3. The method of claim 2 wherein said contact member material is selected from the group consisting of sapphire and diamond.

4. The method of claim 1 wherein said contact member is comprised of a peripheral portion and an interior portion, and wherein said peripheral portion is cooled and said interior portion is in contact with said skin.

5. The method of claim 4 wherein said peripheral portion of said contact member is cooled by coupling said peripheral portion of said contact member to a thermoelectric cooler and heatsink.

6. The method of claim 5 wherein said contact member acts as a intermediate heatsink between said skin and said thermoelectric cooler.

7. The method of claim 1 wherein said contact member is a disk having a diameter of at least 25 mm and a thickness of at least 2 mm.

8. The method of claim 1 wherein said contact member is cooled by circulating a material selected from the group consisting of a cooling gas and a cooling liquid through a channel in at least a portion of said contact member.

9. The method of claim 1 wherein said beam of light is a diode laser.

10. The method of claim 1 wherein said beam of light is at a power level equal to or greater than ten watts.

11. The method of claim 1 further comprising controlling a depth under said skin of a focus of said beam of light.

12. The method of claim 1 wherein said step of scanning said beam of light across said area of sin is performed in accordance with a predetermined pattern.

13. The method of claim 12 wherein said predetermined pattern is a pseudo-random sequence of positions covering substantially all of said area of said skin.

14. The method of claim 12 wherein said predetermined pattern is a pseudo-random sequence of positions within said area of said skin.

15. An apparatus for removing hair from skin comprising:
   (a) a light source for generating a beam of light having a wavelength in the range of 650 nm to 1000 nm and having a spot size;
   (b) a contact member for providing a window for said beam of light to said skin, said contact member having a surface area greater than said spot size of said beam of light and wherein said beam of light has an angle of convergence at said skin of at least 8.5°;
   (c) a scanner for moving said beam of light in a predetermined pattern on said skin through said window; and
   (d) a cooling device for cooling at least a portion of said contact member.

16. The apparatus of claim 15 wherein said light source generates a beam of light at a power level equal to or greater than ten watts.

17. The apparatus of claim 15 wherein said predetermined pattern is a pseudo-random sequence of positions covering substantially all of said surface area.

18. The apparatus of claim 15 wherein said predetermined pattern is a pseudo-random sequence of positions within said surface area.

19. The apparatus or claim 15 wherein said scanner and said light source are connected by an optical fiber.

20. The apparatus of claim 15 wherein said contact member comprises a material which is transparent to wavelengths emitted by said light source and has a high thermal conductivity and capacity.

21. The apparatus of claim 20 wherein said contact member comprises a material selected from the group consisting of sapphire and diamond.

22. The apparatus of claim 15 wherein at least a portion of said contact member is for contacting said skin.

23. The apparatus of claim 15 wherein said contact member comprises a peripheral portion and an interior portion, and wherein said peripheral portion is for cooling and said interior portion is for contacting said skin.

24. The apparatus of claim 23 further comprising a coupling between said peripheral portion of said contact member and a thermoelectric cooler and heatsink.

25. The apparatus of claim 24 wherein said contact member also provides an intermediate heatsink between said skin and said thermoelectric cooler.

26. The apparatus of claim 15 wherein said contact member is a disk having a diameter of at least 25 mm and a thickness of at least 2 mm.

27. The apparatus of claim 15 wherein said scanner includes a lens for controlling a depth under said skin of a focus of said beam of light.

* * * * *